United States Patent [19]
Nguyen

[11] Patent Number: 6,165,190
[45] Date of Patent: Dec. 26, 2000

[54] CAPSULECTOMY DEVICE AND METHOD THEREFORE

[76] Inventor: Nhan Nguyen, 7515 Lehigh St., New Orleans, La. 70127

[21] Appl. No.: 09/323,784

[22] Filed: Jun. 1, 1999

[51] Int. Cl.$^7$ ........................................................ A61F 9/00
[52] U.S. Cl. ............................................ 606/166; 606/171
[58] Field of Search .................................... 600/166, 167, 600/170, 180, 181

[56] References Cited

U.S. PATENT DOCUMENTS

| | | |
|---|---|---|
| 4,180,075 | 12/1979 | Marinoff . |
| 4,423,728 | 1/1984 | Lieberman . |
| 4,570,632 | 2/1986 | Woods . |
| 4,708,318 | 11/1987 | Pzandak . |
| 4,911,161 | 3/1990 | Schechter . |
| 5,261,923 | 11/1993 | Soares . |
| 5,342,377 | 8/1994 | Lazerson . |
| 5,423,841 | 6/1995 | Kornefeld . |
| 5,549,622 | 8/1996 | Ingram ...................................... 606/166 |
| 5,591,185 | 1/1997 | Kilmer et al. ........................... 606/166 |
| 5,792,166 | 8/1998 | Gordon . |
| 5,860,994 | 1/1999 | Yaacobi . |

Primary Examiner—Michael Buiz
Assistant Examiner—Vy Q. Bui
Attorney, Agent, or Firm—Joseph T. Regard, Ltd.

[57] ABSTRACT

A surgical instrument for ophthalmic surgery, allowing the user to form a uniform circular incision of the anterior lens capsule of an eyeball, as part of an anterior capsulotomy. The capsulectomy device of the preferred embodiment of the present invention has first and second ends, with a rotor emanating from one end, the rotor having a cutting blade or bin situated at the distal end of the rotor, the rotor rotating in pivotal fashion up to 360 degrees, while simultaneously reciprocating the cutting blade at a consistent stroke so as to provide optimal incision edge and depth of the anterior lens capsule of the eyeball. The device is hand held and relatively compact, having provided therein a motor and gear reduction/transmission system for driving the rotor and providing the reciprocating action to the cutting blade or pin. The device further includes a power supply, which is illustrated as a separate component fed to the device via wire, as well as controls for initiating power, as well as varying the speed of the motor. Unlike the prior art systems, which generally have relied upon the skill of the surgeon to perform the radial incision by hand, the present system provides a relatively easy and uniform system for performing the radial incision which is believed to be safer, more uniform, and less time consuming than prior techniques.

24 Claims, 9 Drawing Sheets

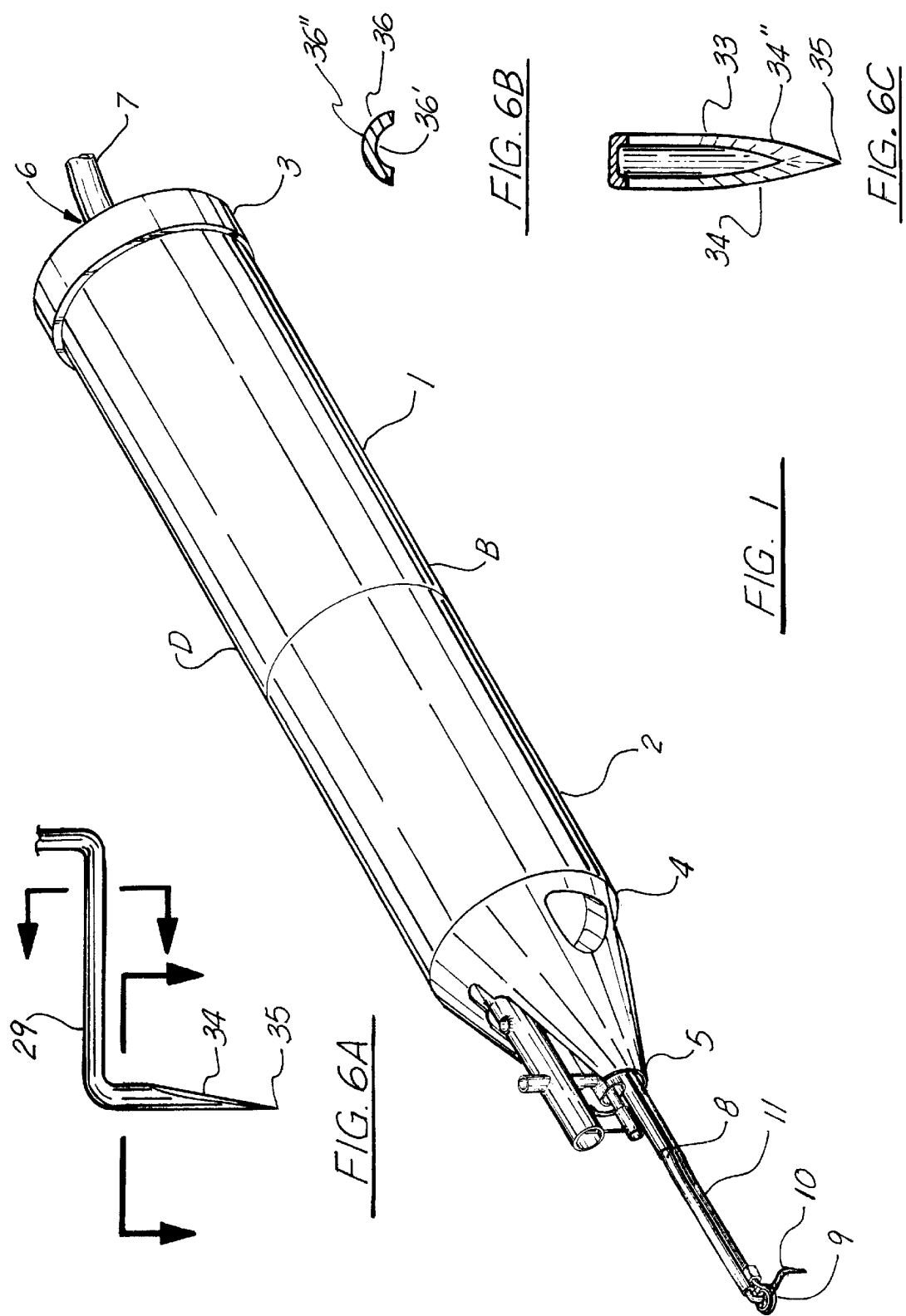

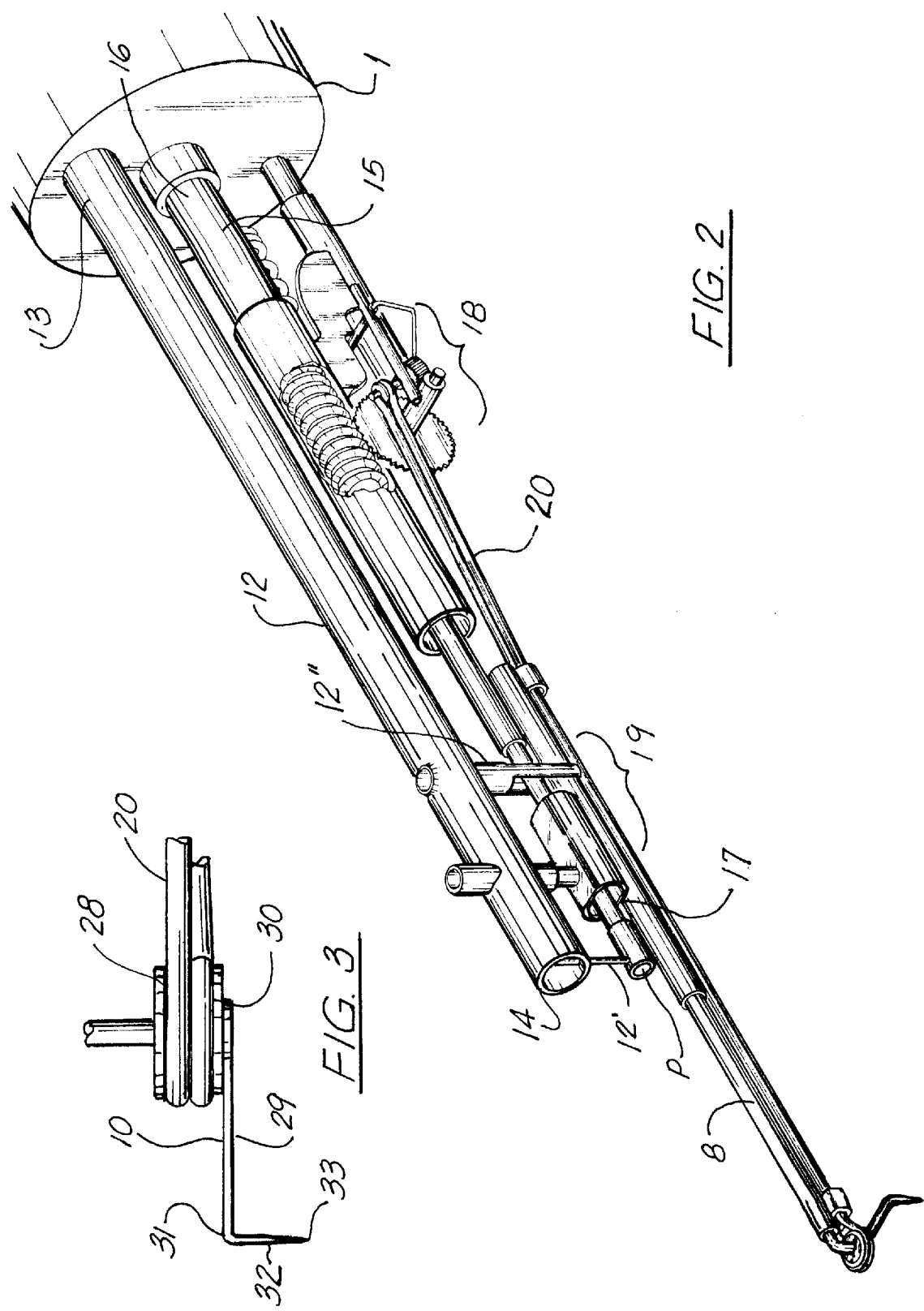

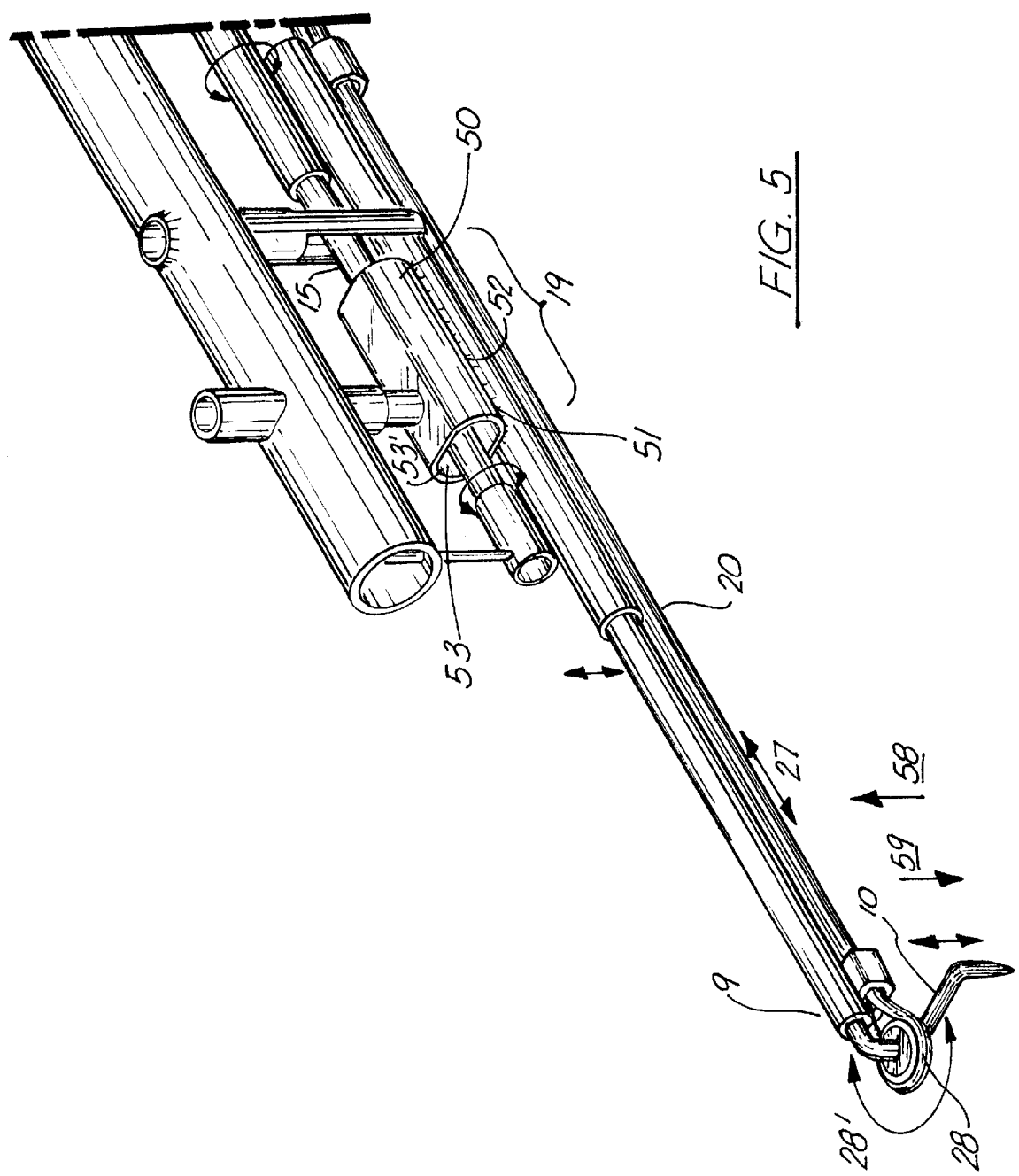

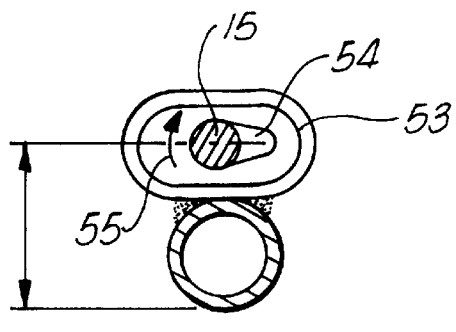
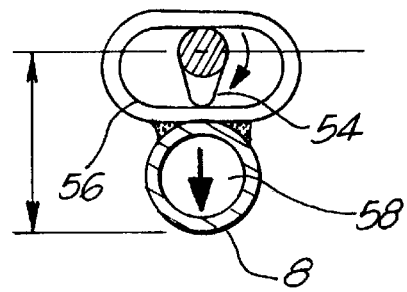
FIG. 7A    FIG. 7B
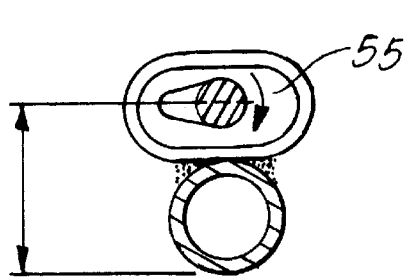
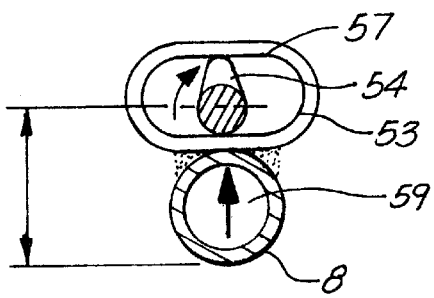
FIG. 7C    FIG. 7D
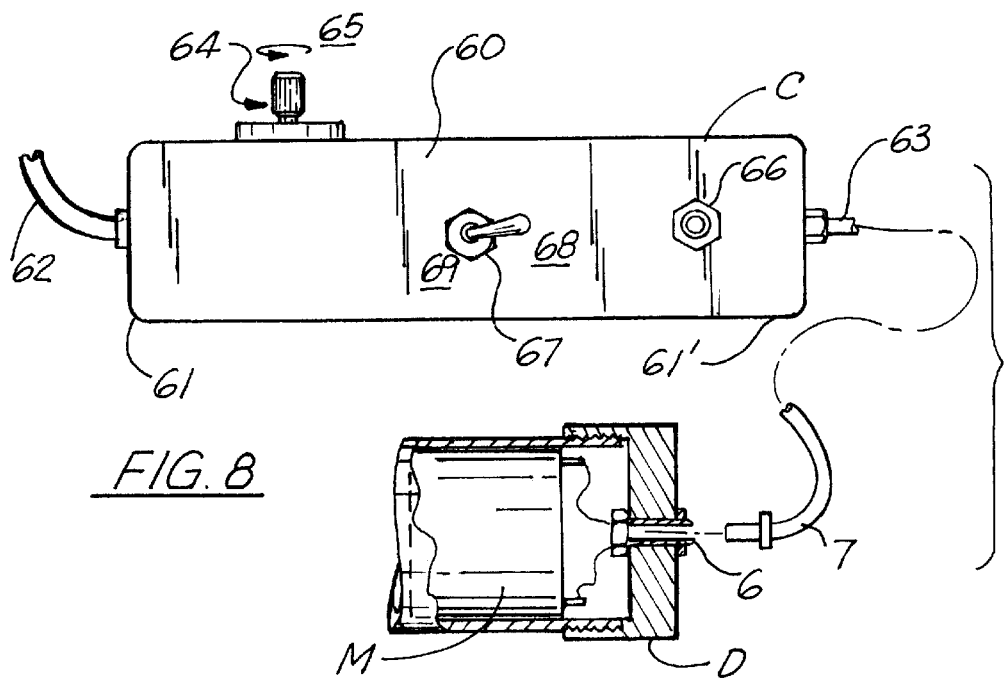
FIG. 8

CAPSULECTOMY DEVICE AND METHOD THEREFORE

TECHNICAL FIELD OF THE INVENTION

The present invention relates to surgical instruments, and in particular to a surgical instrument for ophthalmic surgery, allowing the user to form a uniform circular incision as part of an anterior capsulotomy for replacing a lens damaged by cataracts or the like. The capsulectomy device of the preferred embodiment of the present invention has first and second ends, with a rotor emanating from one end, the rotor having a cutting blade or bin situated at the distal end of the rotor, the rotor rotating in pivotal fashion 360 degrees, while simultaneously reciprocating the cutting blade at a consistent stroke so as to provide optimal incision of the anterior lens capsule of the eyeball.

The device is hand held and relatively compact, having provided therein a motor and gear reduction/transmission system for driving the rotor and providing the reciprocating action to the cutting blade or pin. The device further includes a power supply, which is illustrated as a separate component fed to the device via wire, as well as controls for initiating power, as well as varying the speed of the motor.

The rotating cutting head and extension is small enough to fit through a 3 mm limbal incision, providing an excellent radial incision within the confines of the eyeball, with little operator manipulation.

Unlike the prior art systems, which generally have relied upon the skill of the surgeon to perform the radial incision by hand, the present system therefore provides a relatively easy and uniform system for performing the radial incision which is believed to be safer, more uniform, and less time consuming than prior techniques.

BACKGROUND OF THE INVENTION

While the prior art has taught some varied and diverse devices for performing capsulectomies or the like, some of including rotating blades or other cutting instruments for forming radial incisions, none are believed to teach or suggest the present invention.

A list of patents having some relevance to the present invention is provided below:

| Patent Number | Inventor | Issue Date |
|---|---|---|
| 5862994 | Yaacobi | 01/19/1999 |
| 5848978 | Cecchi | 12/15/1998 |
| 5792166 | Gordon et al | 08/11/1998 |
| 5423841 | Kornefeld | 06/13/1995 |
| 5342377 | Lazerson | 08/30/1994 |
| 5261923 | Soares | 11/16/1993 |
| 4708138 | Pazandak | 11/24/1987 |
| 4911161 | Schechter | 03/27/1990 |
| 4570632 | Lazerson | 02/18/1986 |
| 4423728 | Leiberman | 01/03/1984 |
| 4180075 | Marinoff | 12/25/1979 |
| 1124552 | Suggs | 01/12/1915 |
| 1043408 | De Vilbis | 11/05/1912 |
| 873100 | Skalstad | 12/10/1907 |

U.S. Pat. Nos. 5,860,994 (FIGS. 2, 5, & 6) and 5,261,923 teach devices for capsulectomies or the like which include a cutting blade situated at the end of a rotor or the like to provide a circular incision, although the drive means and actual cutting means is distinguishable from the present invention.

U.S. Pat. No. 4,708,138 teaches a "Rotating Surgical Cutting Knife" which is manually guided to provide a radial incision. U.S. Pat. No. 4,180,075 teaches another manually guided scalpel designed to manually facilitate a radial incision.

U.S. Pat. No. 4,423,728 teaches a rather complex mechanism in the form of a "Cam Guided Trephine" which appears to provide an annular cut, albeit different from that contemplated in the present invention.

U.S. Pat. No. 4,911,161 teaches a transducer driven cutting needle configured to provide an incision for a capsulectomy or the like. U.S. Pat. No. 4,750,632 teaches another device configured to provide a "continuous series of perforations".

While the above prior art systems provide radial cuts, the devices still are believed to require the operator to provide the incision to the appropriate depth, which is generally around 0.5 millimeters. Too shallow, and the incision is not enough; too deep, and the eye may be permanently damaged.

Further, one may argue that the smooth cut of a radial blade or the like which spins a sharp radial edge does not provide as good of an incision for healing as a more rough-edged incision. The inventor is unaware of any prior art which would accomplish the radial cut of the prior art, with automatic depth control, while providing a rough-edged incision for facilitating better healing.

GENERAL SUMMARY DISCUSSION OF THE INVENTION

Unlike the prior art, the present invention contemplates a surgical device which forms a radial incision in the anterior lens capsule of an eyeball, for a capsulectomy or the like at a uniform cut and depth, while providing an optimal incision edge without tears or notches, promoting better healing. The present invention accomplishes this in a device which is relatively easy to use, somewhat cost effective in manufacture, operation, and maintenance.

With the preferred embodiment of the surgical instrument of the present invention, an incision for an anterior capsulectomy is radially formed via a single reciprocating cutting blade or pin having front and rear cutting edges, and a reciprocating stroke of the desired depth of the incision, which may be, for example, about 0.5 millimeters, the cutting end micro-machined to slide through a limbal incision of about, for example, 3 millimeters.

The device of the present invention comprises a body encasing a motor and drive mechanism in the form of a gear reduction array, drive belt, and eccentric shaft which fluctuates in reciprocating fashion, the distal tip of the shaft has laterally emanating therefrom a rotor which communicates with the drive belt, the rotor having downwardly directed therefrom a dual edged cutting blade or "pin" (due to its tiny size, having cutting edges of about 0.5 mm length, and vary, depending upon the application in a range of about 0.1 mm–0.7 mm), configured to form the appropriate diameter radial incision, the reciprocating eccentric shaft providing the stroke for the cutting blade.

The device is compact and comfortably and held in a stable hand-held fashion by the user, and further includes easily operated controls for power, speed, and direction.

Thus, unlike the prior art systems supra, which generally have relied upon the skill of the surgeon to perform the radial incision by hand, the present system provides a relatively easy and uniform system for performing the radial incision which is believed to be safer, more uniform, and quicker to implement, with less complications.

It is therefore an object of the present invention to provide a capsulectomy device which performs a uniform radial incision at the appropriate depth automatically.

It is another object of the present invention to provide a capsulectomy device which includes a cutting tip which fits into a limbal incision of about 3 mm or less.

It is another object of the present invention to provide a device for performing radial incisions which provides an incision edge having better healing properties than prior art devices.

It is another object of the present invention to provide a device for performing radial incisions which is relatively cost effective in operation, sanitary, and easy to maintain.

It is another object of the present invention to provide a device for forming precise radial incisions at a uniform depth and consistent cut.

Lastly, it is an object of the present invention to provide a method and system for forming radial incisions for capsulectomies and other delicate surgeries which is relatively safe, effective, as well as being relatively easy to train a user to implement same.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 1 is an isometric, enlarged side view of the capsulectomy device of the present invention, illustrating the body encasing the motor and drive mechanism, the drive extension emanating therefrom, and the reciprocating cutting head situated at the distal end of the drive shaft.

FIG. 2 is an isometric, partial, close-up view of the capsulectomy device of FIG. 1, illustrating the drive mechanism and cutting head.

FIG. 3 is a close up, side view of the cutting head of the device of FIG. 1, illustrating the rotor and cutting pin or blade.

FIG. 5 is an isometric, partial, close-up view of the capsulectomy device of FIG. 1, illustrating the motion of the various components associated with the drive extension to rotate and reciprocate the cutting head.

FIG. 6A illustrates a close-up, side view of the cutting pin or blade of the invention of FIG. 1.

FIG. 6B illustrates a cross-sectional, close-up view of the cutting portion of the cutting pin or blade of FIG. 6A.

FIG. 6C illustrates a side, partially cross-sectional, close-up view of the cutting portion of the cutting pin or blade of FIG. 6B.

FIG. 7A is an end, cut-away, close up view the drive cam mechanism for reciprocating the cutting head of the invention of FIG. 1.

FIG. 7B illustrates a side, partially cross-sectional, close-up view of the partial movement of the drive cam mechanism of FIG. 7A.

FIG. 7C illustrates a side, partially cross-sectional, close-up view of the partial movement of the drive cam mechanism of FIG. 7A.

FIG. 7D illustrates a side, partially cross-sectional, close-up view of the partial movement of the drive cam mechanism of FIG. 7A.

FIG. 8 illustrates a side, partially cross-sectional, close-up view of the control device for controlling the invention of FIG. 1.

DETAILED DISCUSSION OF THE INVENTION

Figure 4:
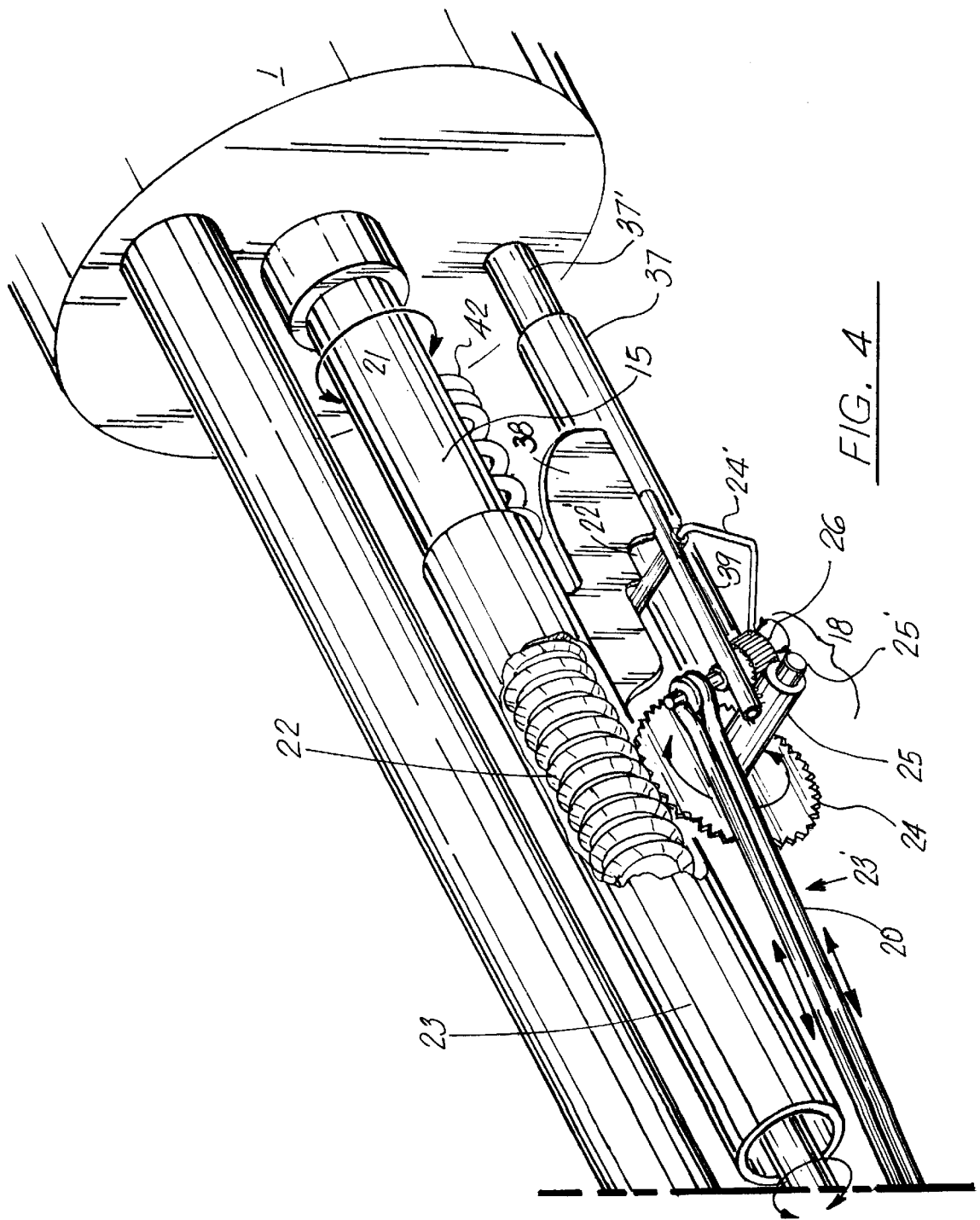
FIG. 4 is an isometric, partially cut-away, close-up view of the drive mechanism of FIG. 2.

Referring to FIGS. 1 and 8 of the drawings, the device D of the present invention comprises a body B including a main housing 1, a removable secondary housing 2, first 4 and second 3 ends, each end having passages 5, 6, formed therein, respectively, passage 5 for the passage of a reciprocating shaft 8 (having its second end 9, distal to body B, including a cutting element 10 projecting laterally therefrom) and passage 6 for the passage of power cord 7 there through, respectively. Situated adjacent to, and along the length of, reciprocating shaft 8 is drive belt 11, configured to drive cutting element 10 via motor M within main housing 1, as will be further shown, infra.

Continuing with FIGS. 1 and 2, which illustrates the device D of the present invention with the secondary housing removed to expose a gear reduction system and drive for the drive belt 11, there is provided a shank 12 having first 13 and second 14 ends, the first end 13 adjacent to the main housing 1, the shank and the reciprocating shaft 8 in generally parallel alignment, the shank having first 12' and second 12" lateral support members directed towards the reciprocating shaft 8.

Also emanating from the main housing 1 is drive shaft 15 (driven by motor M shown in FIG. 8) having first 16 and second 17 ends, the drive shaft also in general parallel alignment with shank 12, the second 17 end of drive shaft supported via pivotal support P, which is engaged to a first 12' lateral support member, the pivotal support P having formed therein a passage having an inner wall diameter greater than the outer diameter of the first 16 end of drive shaft 15, such that the first end 16 of drive shaft 15 is situated within pivotal support P and supported thereby in such a manner as to permit the unimpeded rotation of the drive shaft about its longitudinal axis.

As shown in FIGS. 2, 4, and 5, drive shaft 15 drives a belt drive 18 to drive belt 20 via worm pinion 22 formed along the length of drive shaft 15, the worm pinion meshing 23' with spur gear 24, which is part of belt drive 18, which in turn, turns worm pinion 25 supported by shaft 25', which worm pinion 25 engages cogwheel 26, which is engaged to shaft 26' to drive 27 belt 20 via drive shaft rotation 21, resulting in gear reduction of drive shaft speed with a proportional increase in torque for driving the belt 20. Cogwheel 26 is held in place via tension spring 24'. The tension spring 24' is engaged to support tube 22', which tube is affixed to sleeve 37, which sleeve is telescopingly adjustable along belt drive support 37' (having end 39 which supports belt drive 18) via spring 40, so as to adjust belt tension along drive belt 20. Sleeve 37 also supports shield 23 about worm pinion 22 (except for the area where spur gear 24 meshes with worm pinion 22), via shield support 38.

The belt 20, in turn, is looped around rotor 28 at the end of reciprocating shaft 8, so as to transmit rotation 28' to rotor 28 upon driving 27 of the belt, which rotor communicates with cutting element 10 to rotate same. As shown, cutting element 10 includes pivot member 29 having first 30 and second 31 ends, the first end affixed to the underside of rotor 28, the second end having emanating in lateral fashion a cutting member 32 having cutting tip 33.

Continuing with FIGS. 3, 6A, 6B, and 6C, cutting tip 33 includes a sharp end 35 having tapered therefrom first 34 and second 34" sharp cutting edges, a first face 36' which may have a radially concave wall, and a second face 36", which may have a radially convex wall, for increased structural integrity. In the present, working model of the preferred embodiment of the present invention, the cutting tip of the invention was fabricated from a hypodermic needle, cut longitudinally to split same along its length about 0.5 mm, more or less, up from the pointed tip, with the edges sharpened to form a cutting surface. Because the cutting tip is fashioned from a hypodermic needle, the edges approaching the end are tapered to form the sharp tip. The edges 34, 34" which form the cutting edges present invention, are aligned with the radial path of the rotor, such that the first edge 34 cuts along the radial path formed by rotation of the rotor in clockwise fashion, the second edge 34" cutting with rotation in counter-clockwise fashion.

Continuing with FIGS. 4 and 5, reciprocating shaft 8 is affixed (via weld 52, solder, or the like) at generally its first end 9' a housing 50 having a longitudinal axis in line with the longitudinal axis of the reciprocating shaft 8, the housing having a conduit formed through its length having a elliptical or oval inner wall 53, said inner wall configured to envelope drive shaft 15.

As shown in FIGS. 7A–7D, drive shaft 15 has mounted thereupon a cam 54 configured to engage the inner wall 53 of housing 50 in order to reciprocate housing 50 and thereby reciprocate reciprocating shaft 8 with the rotation of drive shaft 15, thereby providing an eccentric shaft. As shown, with the rotation 55 of drive shaft 15, cam 54 likewise is displaced such that it communicates with the bottom 56 of the inner wall 53, resulting in driving down 58 housing and reciprocating shaft, while additional rotation 55 results in cam 54 engaging the top 57 of inner wall, resulting in upward 59 movement of housing and reciprocating shaft; continued rotation of the drive shaft results thereby in reciprocating movement of reciprocating shaft, which in turn reciprocates the cutting element supported at the second end 9 of the reciprocating shaft, which cutting element, and cutting tip 33 are configured to simultaneously reciprocate via the reciprocating shaft, and rotate via the drive belt, belt drive, and worm pinion arrangement discussed supra., and illustrated in FIG. 5.

Continuing with FIGS. 1 and 8, the device D of the present invention is controlled via controller module C, comprising a enclosure 60 having first 61 and second 61' ends, respectively, having an input power cord 62 and output power cord 63 running there through, respectively. As shown, power is selectively initiated to the output power cord 63 and thereby to power cord 7 to device D, via power button 66, in the preferred embodiment requiring constant pressure for power flow. A rheostat 64, variable resistor, or the like 64 is configured to vary the power to increase or decrease the RPM's of motor M via selective adjustment 65 of the rheostat 64, thereby selectively varying the speed of rotation and reciprocating motion of rotor and cutting blade on device D. Polarity of the power coming into the controller via input power cord 62 via switch 67, selectively varying the direction of rotation of the motor M of device D, thereby varying the direction of rotation of the rotor and cutting blade on said device D; as shown, switch has first a positive polarity 69, clockwise direction setting and a negative polarity 68, counter clockwise direction setting.

With the above, a user is able to utilize the reciprocating, radial traversing path of the cutting blade mounted upon the rotor, driven by the motor, and controlled by the controller module C to perform a delicate and demanding radial incision of the anterior capsule of the lens of the eye for a capsulorhexis or capsulectomy procedure.

Figure 9A:
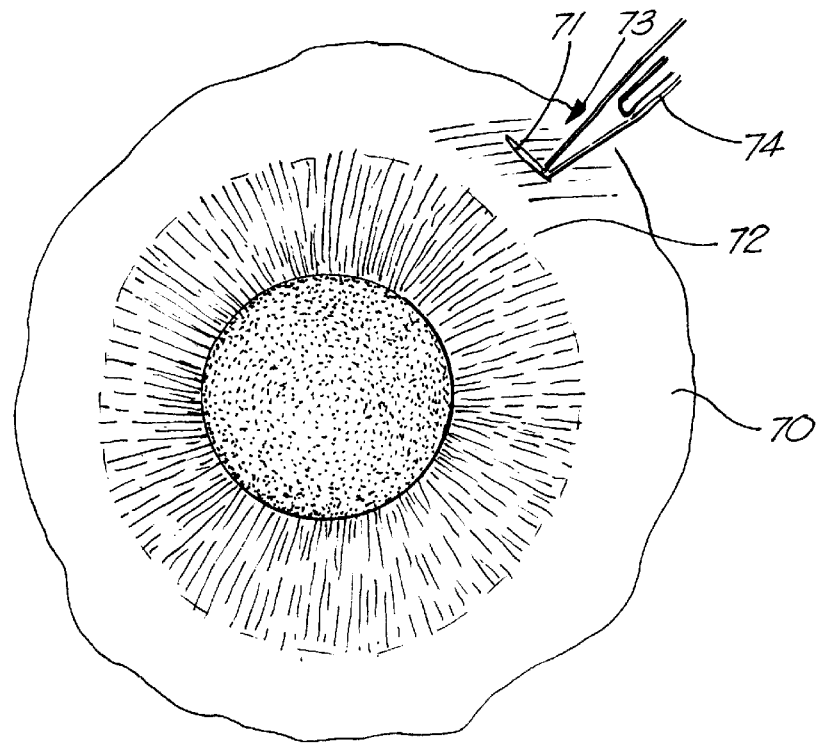
FIG. 9A illustrates a side, partially cross-sectional, close-up view of a first step in the method of capsulectomy of FIG. 1, wherein an incision is made in the vicinity of the meeting of the cornea and sclera.
Figure 9B:
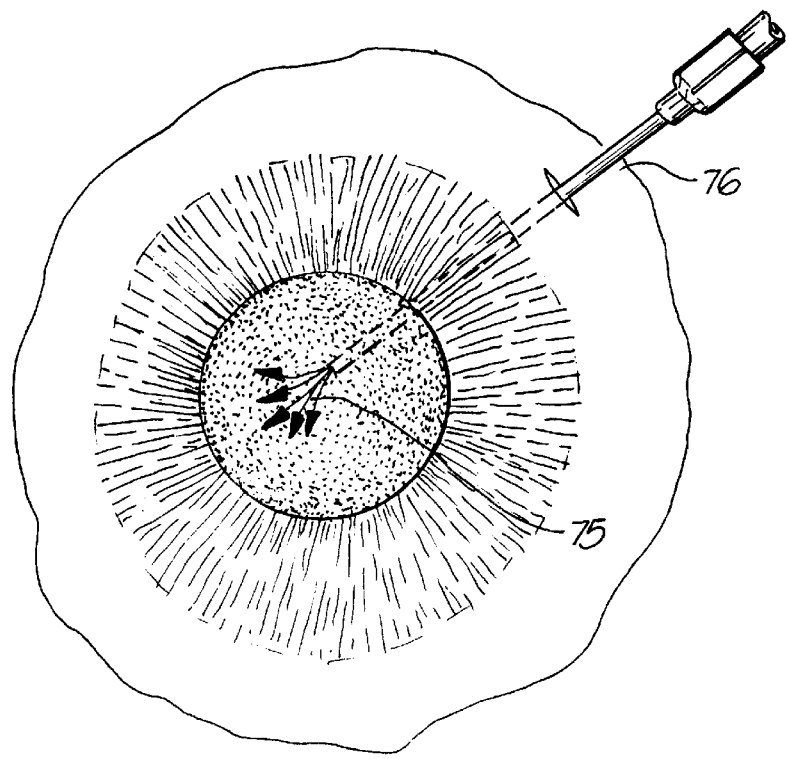
FIG. 9B illustrates a side, partially cross-sectional, close-up view of a second step in the method of capsulectomy of FIG. 9A, wherein the anterior chamber is filled with viscoelastic material.

In an example of use, referring to FIGS. 9A and 9B, a scalpel 74 or the like is used to make an incision 71 (about 3 mm) in the eyeball 70 of the patient, ideally between the cornea 72 and the sclera 73. Saline 75 or some other liquid may be injected into the eyeball via hypodermic needle 76 or the like in such a manner as to raise the cornea, so that the instrument may better pass under the cornea, in order to prevent damage to same during the capularhexis procedure.

Figure 9C:
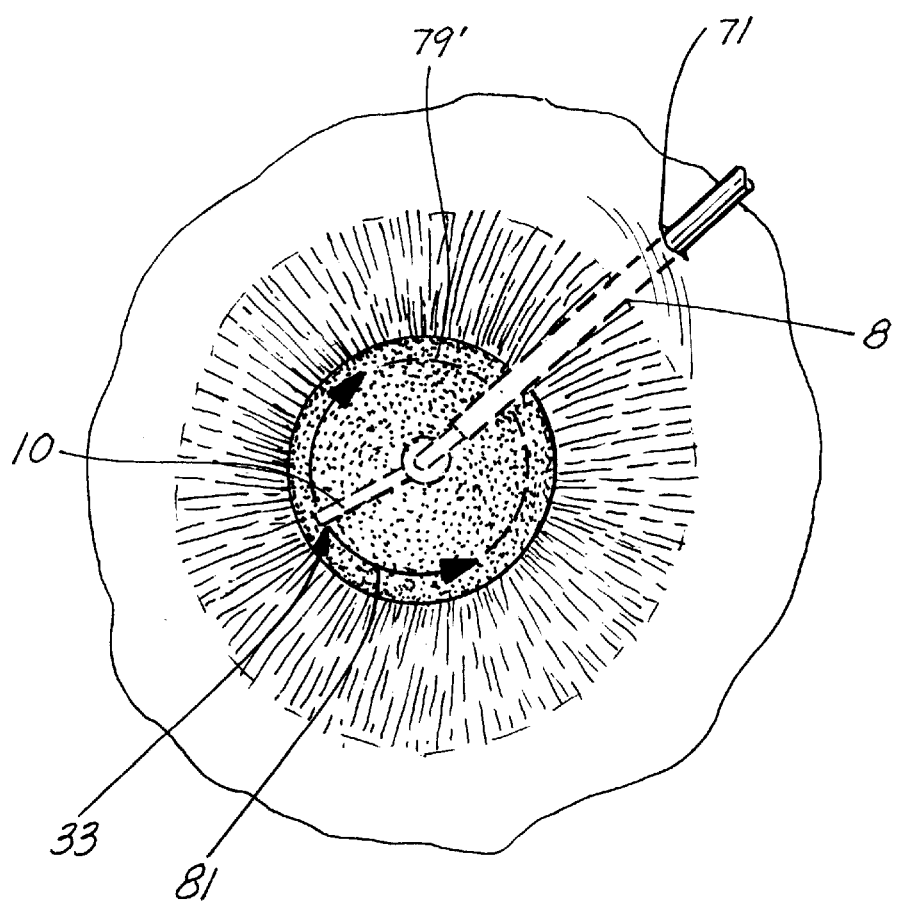
FIG. 9C illustrates a side, partially cross-sectional, close-up view of a third step in the method of capsulectomy of FIG. 9A, wherein the cutting head of the device of FIG. 1 is inserted through the incision, the cutting head then rotated and reciprocated to form a circular incision in the capsule to gain access to the lens.
Figure 10A:
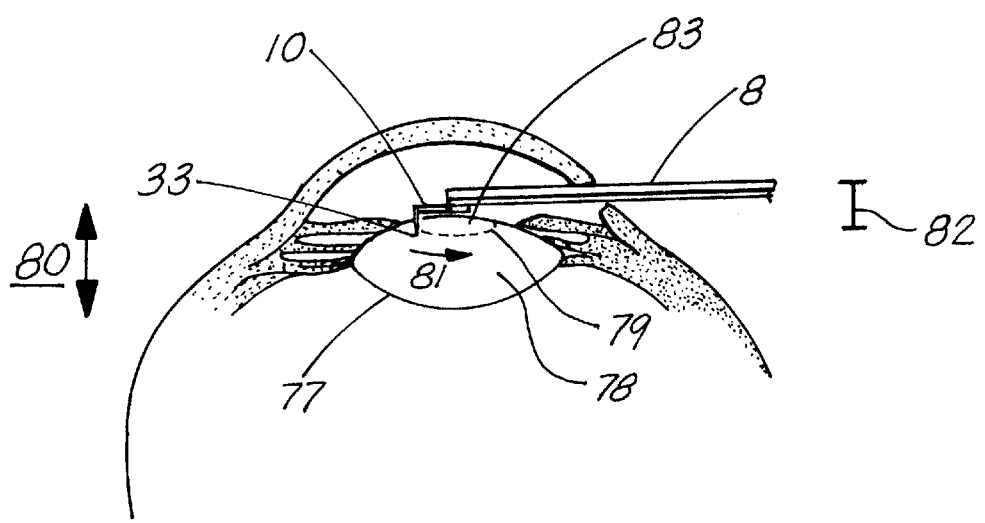
FIG. 10A is a side, partially cross-sectional, close-up, partially cut-away view illustrating of the step of FIG. 9C.

Continuing with FIGS. 8, 9C and 10A, the cutting element 10 of the device of the present invention is held by the body B by the user by grasping same, and the end 9 of the reciprocating shaft 8 having cutting element 10 is then inserted through the incision 71, under the cornea, and the reciprocating shaft 8 passed therein until the rotor 28 is centered above the anterior 78 portion of the lens capsule 77, with the cutting tip 33 contacting the anterior of the lens capsule at about it's exposed periphery. The user then adjust the console controls to the desired direction (clockwise or counterclockwise) and speed, then initiates power to the motor M via power button 66, causing the cutting tip 33 to reciprocate 80 at the predesignated stroke 82, or desired cutting depth, while traversing 81 a radial path, forming a radial cut 79 without tears or notches. Preferably, the cutting tip forms a circular, 360 degree radial cut 79'.

Figure 10B:
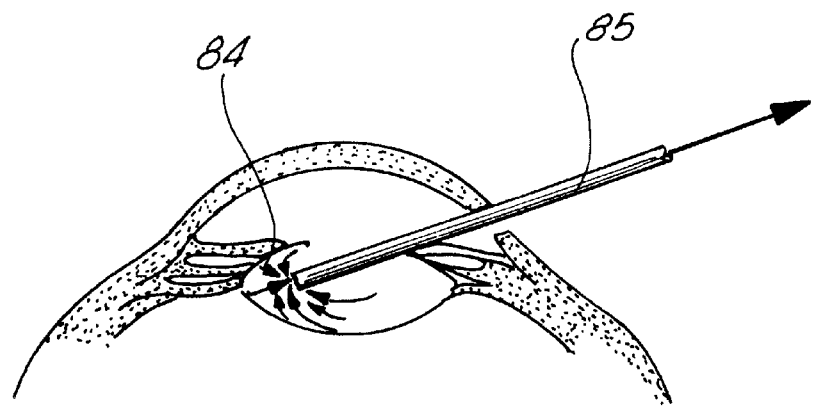
FIG. 10B is a side, partially cross-sectional, close-up, partially cut-away view of the invention of FIG. 10A illustrating a probe suctioning out the lens.

A phaco probe may then be used to fragment (via prechopper, ultrasonic technique, or the like) the harder lens nucleus, which resulting fragments are then suctioned out. An irrigation aspiration (IA) probe may be used to remove the epi-nucleus, incised anterior capsule, and cortex, as shown in FIG. 10B. If the phacoemulsification technique is not employed, another technique, such as extracapsular extraction may be employed, wherein the lens nucleus is not fragmented prior to extraction. However, this technique requires a larger incision in the eyeball to accommodate the whole nucleus, and results in more trauma to the eyeball. Once the fragmented material is suctioned from the area, the intraocular lens (IOL) is ready for insertion.

Figure 10C:
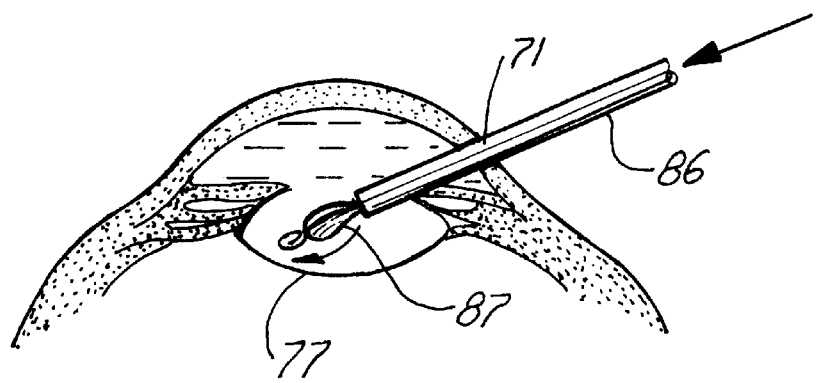
FIG. 10C is a side, partially cross-sectional, close-up, partially cut-away view of the invention of FIG. 10A illustrating the third step of inserting an intraocular lens into the lens capsule.
Figure 10D:
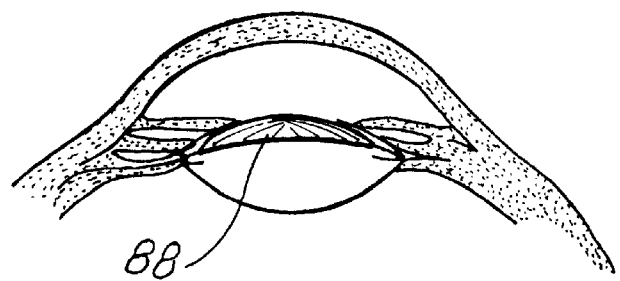
FIG. 10D is a side, partially cross-sectional, close-up, partially cut-away view of the invention of FIG. 10A illustrating the eye with the replacement lens.

Utilizing a conventional technique and instruments, the IOL is inserted 87 through the incision 71 through the radial incision, and into the lens capsule 77 via a tube 86 through the incision, where the lens 88 is allowed to unfurl into position generally within the lens capsule, as shown in FIGS. 10C and 10D.

Figure 6D:
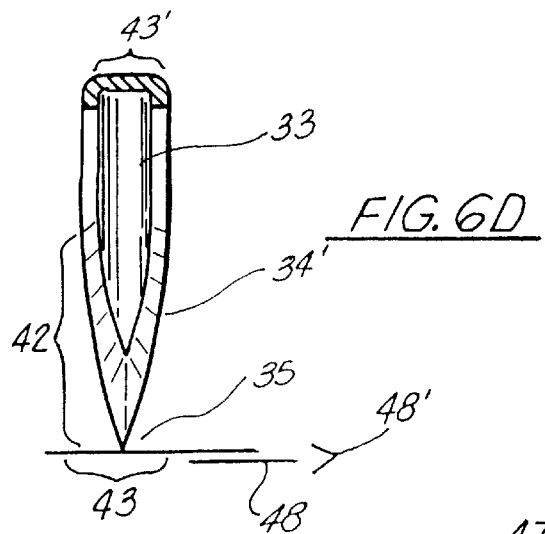
FIG. 6D illustrates a side, partially cross-sectional, close-up view of the cutting portion of the cutting pin or blade of FIG. 6B, as situated adjacent to the membrane to be incised.
Figure 6E:
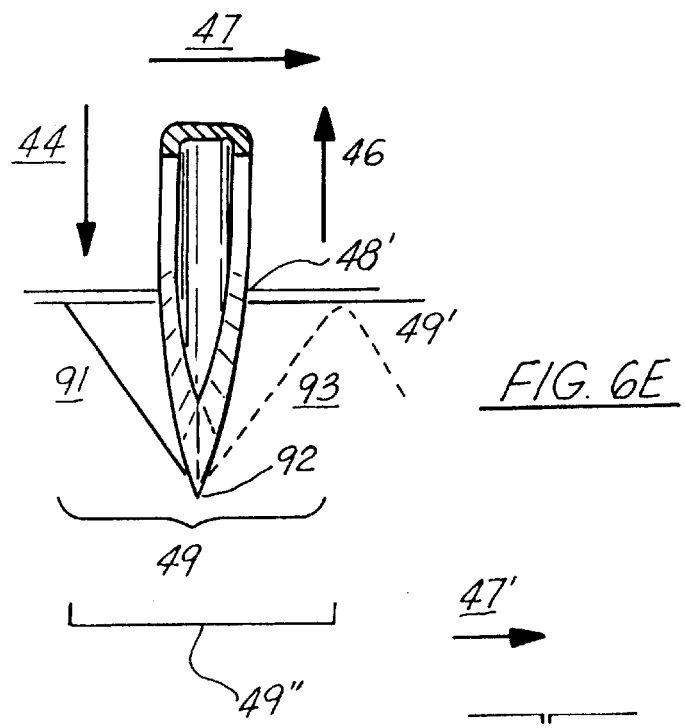
FIG. 6E illustrates a side, partially cross-sectional, close-up view of the cutting portion of the cutting pin or blade of FIG. 6D, illustrating the cutting tip cutting the anterior capsule membrane, illustrating the path of same.
Figure 6F:
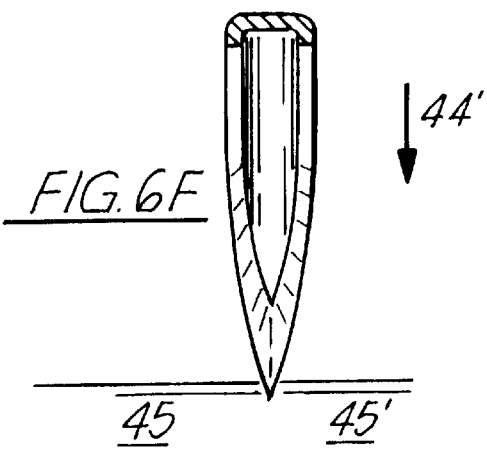
FIG. 6F illustrates a side, partially cross-sectional, close-up view of the cutting portion of the cutting pin or blade of FIG. 6E, illustrating the cutting tip having cut a portion of the anterior capsule membrane, and in the process of proceeding to perform further incision of same, and illustrating the path of same.

As one will note in the above disclosure, the mechanism of the present invention does not provide a short rotational movement of the hub and blade, then a pause with a reciprocation of the cutting blade, then short rotational movement, etc. Rather, as shown in FIGS. 6D, 6E, and 6F, the forms the incision in a continuous rotational movement with corresponding reciprocation of the blade, thereby following a vertical "zig-zag" path, whose depth of incision varies to some degree. Nonetheless, the purpose of the incision is to cut through the anterior capsule membrane, which is only about 0.02 mm thick, while the total vertical stroke of the reciprocating blade is some 0.5 mm, so, even at its shallowest incision point, the anterior capsule membrane is fully severed. This "zig-zag" vertical motion is due to the fact that the cam unit forming the reciprocating action of the reciprocating shaft and the belt drive (18) are linked to the same drive shaft. This "zig-zag" movement provides for an traversing angled stroke which provides a better severing action, and thereby a cleaner cut forming the incision.

As shown in FIG. 6D, the maximum width 43 of the cutting edges 34, 34', corresponds to about the width 43' of the cutting tip 33, while the length of each cutting edge is about 0.5 mm. As indicated, the membrane 48 of the anterior capsule to be incised is only about 0.02 mm thick 48'.

Continuing with the FIGS. 6D, 6E, and 6F, in forming the incision, after aligning the unit as discussed above, the tip 35 is placed against the membrane 48, and the power applied to energize the motor, reciprocating the cutting tip and slowly rotating same. As shown, the cutting tip is reciprocated down 44 as it is traverses 47 slightly along its radial path via the hub, forming a downwardly angled 91 penetration to the bottom 92 of the reciprocating path, about 0.5 mm deep, more or less (anticipated range of about, for example, 0.1 mm–0.7 mm), then an upwardly angled 93 retraction of the cutting tip, the continuous motion in traversing 47 along the path, coupled with the down 44 then up 46 reciprocating action, providing a application of the leading cutting edge (34' in FIG. 6D) against the membrane (48 in FIG. 6D), in a sawing fashion, providing a clean cut or incision of said membrane, which sawing action is repeated 49' with the next stroke 44', forming further incision 45' communicating with the previous incision 45, and so forth until rotor supporting the cutting tip traverses a full revolution, indicative of the radial incision having completed a 360° path, and thereby complete.

As shown, the full stroke 46 of the cutting tip comprises a downward 44 then upward 46, vertical reciprocating movement, coupled with traversal 47 of the leading cutting edge upon its path, providing an incision length per up/down cycle of approximately 5 mm.

Exemplary Specifications

Motor Voltage: 3 Volts D.C.
Operational Range (RPM): about 1,000–3,000.
Cutting Blade Length: 0.5 mm; pitch, about thirty degrees (30°)
Anticipated Operational RPM Range: About 1,000–3,000.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

Elements of the Invention

D Device
B Body
C Controller Module
P pivot member
M motor
1 main housing
2 secondary housing
3 second end
4 first end
5 passage
6 passage
7 power cord
8 reciprocating shaft
9 end
10 cutting element
11 drive belt
12,' shank
13 first end
14 second end
15 drive shaft
16 first end
17 second end
18 belt drive
19 reciprocating shaft drive
20 belt
21 rotates
22 worm pinion
22' pivotal support
37,' sleeve support
38 shield support
39 belt drive support
23 shield
24 spur gear
24' tension spring
23' bias spur gear towards worm pinion
25 worm pinion
25' shaft
26 cogwheel
26' shaft
27 drives belt
28 rotor
28' rotates
29 pivot member
30 first end
31 second end
32 cutting member
33 cutting tip
34 cutting edge
34' cutting edge 35 tip
36 radial support wall
(see above)
40 drive belt tension spring
41
42 length of cutting edge
43 longitudinal width of cutting surface
43' width of cutting blade
44,44' downstroke
45,' first, second incision strokes
46 upstroke
47,' travel
48,' depth of anterior chamber membrane (0.02 mm), ',depth of incision (0.5 mm)
49,' incision stroke, next stroke
50 housing envelopes driveshaft 15
51 engaged to reciprocating shaft 8
52 via weld, solder, or other bond
53 conduit with ellipsoidal or oval walls
54 cam
55 rotation
56 bottom inner wall of ellipsoidal conduit
57 top inner wall of ellipsoidal conduit
58 drive down reciprocating shaft 8
59 drive up reciprocating shaft 8
60 enclosure
61 first end, 61' second end
62 power cord in
63 power cord out
64 rehostat or variable resistor
65 rotation
66 power button
67 direction switch
68 clockwise position
69 counterclockwise position
70 eyeball
71 limbal incision 0.3 mm where the cornea and sclera meet
72 cornea
73 sclera
74 scalpel
75 saline
76 hypodermic needle
77 lens capsule
78 anterior lens capsule
79 radial cut
80 reciprocating action
81 radial movement
82 0.5 mm stroke
83 radial portion of anterior capsule incised from capsule
84 suction of incised anterior capsule and epi nucleous and cortex portion, fragmented crystelline nucleous (may be by phaco probe)
85 irrigation-aspiration probe
86 tube
87 insertion of intraocular lens (IOL)
88 IOL inserted in eye
89 inserted
90
91 angled penetration
92 bottom penetration
93 angled removal

What is claimed is:

1. A surgical instrument for forming a radial incision, comprising:
a user supported reciprocating shaft having first and second ends, said second end of said reciprocating shaft having situated thereupon rotation means for providing rotation, said rotation means having mounted thereupon, in lateral fashion, a cutting blade having a cutting tip and a leading cutting edge, said cutting blade mounted upon said rotation means such that a single rotation of said rotation means traverses said leading cutting edge of said cutting blade along a complete path for forming the radial incision;
reciprocation means for reciprocating said reciprocating shaft, such that reciprocation of said reciprocating shaft reciprocates said cutting blade as said rotation means rotates.

2. The surgical instrument of claim 1, wherein said reciprocation means comprises a motor driven drive shaft having a cam situated thereupon, said cam communicating with a housing mounted upon said reciprocating shaft in reciprocating fashion.

3. The surgical instrument of claim 2, wherein said rotation means comprises a rotating hub mounted to said second end of said reciprocating shaft, said hub driven by a drive belt driven by said drive shaft.

4. The surgical instrument of claim 3, wherein a motor is housed in a main housing, and said reciprocating shaft is supported by the user by grasping said main housing.

5. The surgical instrument of claim 4, wherein said cutting blade has first and second cutting edges terminating in said cutting tip, said first cutting edge forming said leading cutting edge when said cutting tip is rotated in a clockwise direction via said hub, said second cutting edge forming said leading cutting edge when said cutting tip is rotated in a counterclockwise direction via said hub.

6. The surgical instrument of claim 5, wherein said belt is driven by said belt shaft by a gear reduction array comprising a worm pinion mounted longitudinally upon said drive shaft, a spur gear meshing with said worm pinion, said spur gear having an axle having a second worm pinion situated thereupon, which second worm pinion engages a cogwheel, which cogwheel has a second shaft, which second shaft engages said drive belt to drive same, thereby driving rotating hub.

7. The surgical instrument of claim 7, wherein said first and second cutting edges of said cutting blade have a length of 5 mm or less.

8. The surgical instrument of claim 8, wherein said cutting tip is reciprocated so as to form a stroke of 0.5 mm or less.

9. The surgical instrument of claim 6, wherein said cutting tip has a first face comprising a radially concave wall, and a second face comprising a radially convex wall.

10. The surgical instrument of claim 6, wherein said first and second cutting edges taper to a pointed tip.

11. The method of incising the anterior membrane of a lens capsule of an eyeball having a cornea, sclera, and lens, comprising the steps of:
a. providing an ophthalmic surgical instrument, comprising:
a user supported reciprocating shaft having first and second ends, said second end of said reciprocating having situated thereupon rotation means for providing rotation, said rotation means having mounted thereupon, in lateral fashion, a cutting blade having a cutting tip and a leading cutting edge, said cutting blade mounted upon said rotation means such that a single rotation of said rotation means traverses said leading cutting edge of said cutting blade along a complete path for forming a radial incision;
reciprocation means for reciprocating said reciprocating shaft, such that reciprocation of said reciprocating shaft reciprocates said cutting blade as said rotation means rotates;

b. forming an incision on the eyeball generally between the cornea and the sclera;

c. passing said second end of said reciprocating shaft into said incision such that said rotating means and said cutting blade are situated under the cornea;

d. centering said rotating means above the anterior membrane of the lens capsule, while placing said cutting tip of said cutting blade in contact with said anterior membrane of said lens capsule;

e. reciprocating said cutting blade into said anterior membrane of said lens capsule, incising said lens capsule, while rotating said rotation means to traverse said reciprocating cutting blade along a radial path, forming a radial incision of said anterior membrane of said lens capsule.

12. The method of claim 11, wherein there is further provided, after step "a", the step of injecting fluid under the cornea to raise same.

13. The method of claim 12, wherein there is further provided, after step "e", the additional step "f" of fragmenting the lens and suctioning said fragmented lens and radial incision.

14. The method of claim 13, wherein there is further provided the step, after step "f" of inserting an intraocular lens through said radial incision, and into said lens capsule.

15. The method of incising tissue, comprising steps of:

a. providing a surgical instrument having first and second ends, said second end of said surgical instrument comprising a reciprocating shaft having emanating therefrom a cutting blade having a cutting edge, said cutting blade pivotally mounted to said reciprocating shaft such that said cutting blade pivots in a circular path; said surgical instrument further comprising reciprocating means to reciprocate said cutting blade, and rotation means to pivotally rotate said cutting blade;

b. manually grasping said first end of said surgical instrument;

c. placing said cutting blade into contact with said tissue;

d. while holding said surgical instrument still, initiating reciprocating means to reciprocate said cutting blade, while e. initiating said rotation means to rotate said cutting edge of said cutting blade along a circular path;

f. forming a radial incision.

16. A surgical instrument for radially incising the anterior lens capsule of an eyeball, comprising:

a user supported reciprocating shaft having first and second ends, said second end of said reciprocating shaft having situated thereupon rotation means for providing rotation, said rotation means having mounted thereupon, in lateral fashion, a cutting blade having a cutting tip and a leading cutting edge, said cutting blade mounted upon said rotation means such that a single rotation of said rotation means traverses said leading cutting edge of said cutting blade along a complete path so as to form a radial incision;

reciprocation means associated with said rotation means for reciprocating said reciprocating shaft, such that reciprocation of said reciprocating shaft reciprocates said cutting blade as said rotation means rotates, said reciprocation means comprising a motor driven drive shaft having a cam situated thereupon, said cam having formed thereabout a housing having an elliptical wall formed therein, said housing mounted upon said reciprocating shaft, said cam configured to engage said elliptical wall of said housing such that rotation of said cam about said drive shaft reciprocates said housing, so as to reciprocate said reciprocating shaft, so as to reciprocate said cutting blade.

17. The surgical instrument of claim 16, wherein said rotation means comprises a rotating hub mounted to said second end of said reciprocating shaft, said hub driven by a drive belt driven by said drive shaft.

18. The surgical instrument of claim 17, wherein a motor is housed in a main housing, and said reciprocating shaft is supported by the user by grasping said main housing.

19. The surgical instrument of claim 18, wherein said cutting blade has first and second cutting edges terminating in said cutting tip, said first cutting edge forming said leading cutting edge when said cutting tip is rotated in a clockwise direction via said hub, said second cutting edge forming said leading cutting edge when said cutting tip is rotated in a counterclockwise direction via said hub.

20. The surgical instrument of claim 19, wherein said belt is driven by said drive shaft by a gear reduction array comprising a worm pinion mounted longitudinally upon said belt shaft, a spur gear meshing with said worm pinion, said spur gear having an axle having a second worm pinion situated thereupon, which second worm pinion engages a cogwheel, which cogwheel has a second shaft, which second shaft engages said drive belt to drive same, thereby driving rotating hub.

21. The surgical instrument of claim 20, wherein said first and second cutting edges of said cutting blade have a length of 5 mm or less.

22. The surgical instrument of claim 21, wherein said cutting tip is reciprocated so as to form a stroke of 0.5 mm or less.

23. The surgical instrument of claim 22, wherein said cutting tip has a first face comprising a radially concave wall, and a second face comprising a radially convex wall.

24. The surgical instrument of claim 23, wherein said first and second cutting edges taper to a pointed tip.

* * * * *